United States Patent
Nisch et al.

(10) Patent No.: US 6,804,560 B2
(45) Date of Patent: Oct. 12, 2004

(54) RETINA IMPLANT

(75) Inventors: Wilfried Nisch, Tübingen (DE); Alfred Stett, Teutlingen (DE); Markus Schubert, Tübingen (DE); Michael Graf, Leonberg (DE); Heinz Gerhard Graf, Magstadt (DE); Hugo Hammerle, Tübingen (DE); Eberhart Zrenner, Tübingen (DE); Martin Stelzle, Reutlingen (DE)

(73) Assignee: Eberhard-Karls-Universitat Tubingen Universitatsklinikum, Tubingen (DE)

( * ) Notice: Subject to any disclaimer, the term of this patent is extended or adjusted under 35 U.S.C. 154(b) by 199 days.

(21) Appl. No.: 10/011,451

(22) Filed: Nov. 7, 2001

(65) Prior Publication Data

US 2002/0177895 A1 Nov. 28, 2002

Related U.S. Application Data

(63) Continuation-in-part of application No. PCT/EP00/03957, filed on May 3, 2000.

(30) Foreign Application Priority Data

May 7, 1999 (DE) .......................................... 199 21 399

(51) Int. Cl.[7] .................................................. A61N 1/18
(52) U.S. Cl. ....................................................... 607/54
(58) Field of Search ............................. 607/54, 53, 61, 607/1, 88, 95; 623/6.63

(56) References Cited

U.S. PATENT DOCUMENTS

| | | | |
|---|---|---|---|
| 4,628,933 A | 12/1986 | Michelson | |
| 5,109,844 A | 5/1992 | de Juan, Jr. et al. | |
| 5,935,155 A | * 8/1999 | Humayun et al. | 607/54 |
| 6,298,270 B1 | 10/2001 | Nisch et al. | |
| 6,683,645 B1 | * 1/2004 | Collins et al. | 348/294 |

FOREIGN PATENT DOCUMENTS

| | | |
|---|---|---|
| DE | 197 05 987 A1 | 5/1998 |
| EP | 0 460 320 A2 | 12/1991 |
| WO | 96/39221 | 12/1996 |
| WO | 09/17343 | 4/1998 |
| WO | 98/17344 | 4/1998 |
| WO | 00/67838 | 11/2000 |

* cited by examiner

*Primary Examiner*—Kennedy Schaetzle
(74) *Attorney, Agent, or Firm*—Knobbe, Martens, Olson & Bear, LLP

(57) ABSTRACT

A retina implant, comprises a surface and a plurality of pixel elements disposed on the surface for receiving and converting incoming light energy into electric energy. At least one amplifier is provided in the implant, and a plurality of stimulation electrodes supplied via the at least one amplifier as a function of signals received by the pixel elements. At least one light-sensitive reference element is coupled with the at least one amplifier for controlling amplification thereof as a function of light energy impinging on the at least one reference element.

31 Claims, 2 Drawing Sheets

RETINA IMPLANT

RELATED APPLICATIONS

This application is a continuation-in-part of the PCT application PCT/EP00/03957 filed May 3, 2000 entitled "RETINA IMPLANT" and claims the benefit of the German Application 199 21 399.2 filed May 7, 1999.

FIELD OF THE INVENTION

The invention is related to a retina implant, comprising a surface with a plurality of pixel elements disposed thereon for receiving and converting incoming light energy into electric energy, at least one amplifier and a plurality of stimulation electrodes being supplied via the at least one amplifier as a function of the signals received by the pixel elements.

BACKGROUND OF THE INVENTION

A retina implant of the afore-specified kind is disclosed in U.S. Pat. No. 4,628,933.

This prior art retina implant is a so-called epiretinal implant which is placed onto the surface of the retina. Essentially it consists of a chip with a plurality of light-sensitive elements being provided on a surface thereof facing the lens of the eye, and converting the image projected through the lens into corresponding electric signals which shall stimulate the photoreceptors disposed in the retina. The individual electric signals received by the light-sensitive elements may be amplified in order to supply associated stimulation electrodes disposed on the rear side of the chip which are provided for stimulating the retina cells.

Due to inherent disadvantages of this system, the recent development has taught away from epiretinal implants and has suggested subretinal implants which are implanted into lower retina layers. A subretinal implant of that kind is disclosed, for example, in WO 98/17343.

This prior art subretinal retina implant comprises a plurality of light-sensitive pixel elements disposed on its surface facing the lens. The pixel elements convert the image incoming through the lens into corresponding electric signals. With the aid of infrared radiation being additionally irradiated into the eye for energy supply purposes via a photovoltaic layer positioned behind the pixel elements, the electric signals are converted into electric stimulating signals. These stimulating signals are fed to the adjacent retina cells via stimulation electrodes which likewise are disposed on the surface of the implant facing the lens.

For epiretinal as well as for subretinal implants it has turned out that it is necessary to couple external energy into the implants in order to convert the incoming light signals into corresponding electrical stimuli being of sufficient stimulation for the cells adjacent the implant. Besides the coupling of invisible infrared light, also other options for coupling energy have been described, for example the option of coupling rf energy via a coil or by utilizing an external battery or an implanted battery.

However, with prior art retina implants a problem has come up, namely the difficulty to convert the incoming light energy into corresponding electrical stimulating signals approximately linearly over a wide intensity range which under natural fluctuations of light intensity may span over various decades.

It is, therefore, an object underlying the invention to provide an improved retina implant allowing the conversion of incoming light energy into appropriate electrical stimulating signals over an intensity range as wide as possible.

SUMMARY OF THE INVENTION

According to the implant specified at the outset, this object is achieved by at least one light-sensitive reference element being coupled with the at least one amplifier for controlling the amplification thereof as a function of the light energy impinging on the at least one reference element.

By doing so, the discharged electrical stimulating signals may be adapted to an average light intensity, as is done also in the course of natural adaptation of the eye relative to a change in ambient light conditions. Hence, it is avoided on the one hand that under relatively bright ambient light the stimulating electrodes transmit too strong electric signals to the adjacent retina cells, which would result in an over-stimulation or even in a damage on these cells. On the other hand, under very weak ambient light conditions, it becomes possible to transmit stimulating signals of sufficient intensity to the adjoining retina cells, so that a substantially improved viewing aid may be offered to a patient even under varying ambient light conditions.

The at least one reference element should, as a matter of fact, be provided with at least a surface area being larger than the surface area of an individual pixel element, or a plurality of reference elements should be provided allowing an averaging over a selected portion of the surface. The at least one reference element, therefore, is the standard for determining the operational range of the individual pixel elements or the amplification characteristic curve is shifted as a function of the mean luminescence intensity.

The size of the at least one reference element depends on which surface portion the average light intensity shall be determined. The size may, therefore, vary between a few $\mu$m and a few mm$^2$.

In a preferred embodiment of the invention, a common reference element is provided extending over a selective portion of the surface with the pixel elements being disposed on the reference element as isolated areas, preferably along a grid pattern.

This feature enables a relatively simple design and the possibility of adaptation to the entire mean light intensity.

According to another variation of the invention, a plurality of reference elements is distributed over a selected portion of the surface along a predetermined pattern between the pixel elements.

By doing so, a special characteristic during the determination of the mean light intensity may be achieved that can be also adapted to the personal physiological conditions of the patient.

According to a modification of this embodiment, the reference elements are distributed over a selected portion of the surface as stripes and/or as a rectangular or an oblique grid.

Such an arrangement allows different variations for the determination of the mean light intensity which, on the one hand, allow a simple design and on the other hand an optimum adaptation to predetermined parameters.

According to the number, arrangement and circuitry of the reference elements, one reference element each may be associated to a plurality of pixel elements, or each pixel element may have one reference element associated thereto, or one pixel element may have a plurality of reference elements associated thereto.

According to another preferred embodiment of the invention, each pixel element has an amplifier and a stimulation electrode associated thereto.

This makes it possible to utilize the light signals received by the individual pixel elements with an utmost resolution for stimulating adjacent cells.

According to another modification of the invention, the reference elements are distributed as stripes over a selected portion of the surface, further reference elements being disposed between the individual stripes and the pixel elements.

This, too, allows an optimum adaptation to predetermined external or physiological parameters of the patient.

According to still another embodiment of the invention, a plurality of reference elements is distributed over a selected portion of the surface in a chessboard pattern, wherein each pixel element is surrounded by a plurality of reference elements arranged at an angle with respect to each other.

When doing so, the reference elements may have a larger length or width as compared to the associated pixel elements, depending on the particularly selected geometrical arrangement, or may be subdivided into individual segments associated to an individual pixel element.

By doing so, it is possible to let selected portions of the surface overlap which are required for the determination of the reference signal for an individual pixel element. Several reference elements or several segments of a reference element, respectively, may be associated to a pixel element in order to determine the mean light intensity over a larger portion of the surface. On the other hand it is also possible that individual reference elements distributed over a larger selected portion of the surface are used as a reference for a plurality of pixel elements or for the entire retina implant.

In such a manner, chip segments are generated utilizing the entire surface of the retina implant for determining the mean light intensity so that if a reference element should become inoperative, only a portion of the retina implant would lose its operability.

According to still another embodiment of the invention, the at least one amplifier amplifies the difference between the output signals of the pixel elements and of the associated reference elements, and controls the associated stimulation electrodes as a function of the amplified signals.

This results in a particularly simple and reliable design of the amplifier circuit. No further averaging means or the like are required.

According to still another embodiment of the invention, the pixel elements and the at least one reference element have the same wavelength sensitivity.

By doing so, the at least one reference element may directly be used for determining the operational range of the prevailing amplifier.

According to another embodiment of the invention, the pixel elements and the at least one reference element are configured as photodiodes.

Appropriate methods for manufacturing same are well-known, allowing a regular arrangement of a high number of pixel elements in an array having a high packing density.

The amplifier or amplifiers may have a linear or a logarithmic characteristic curve.

The utilization of amplifiers having a logarithmic characteristic curve may be advantageous because even in a situation with a large variation of the input signals over a wide intensity range, the output signals only vary over a relatively small range.

It goes without saying that the features mentioned before and those that will be mentioned hereinafter may not only be used in the particularly given combination, but also in other combinations or alone, without leaving the scope of the present invention.

BRIEF DESCRIPTION OF THE DRAWINGS

Further features and advantages of the invention will become apparent from the subsequent description of preferred embodiments with reference to the drawing.

FIG. 3 is a schematic depiction of a top plan view on the surface of the retina implant from which a first conceivable arrangement of pixel elements, amplifiers with stimulating electrodes and a common reference element become apparent;

FIG. 3a is a schematic depiction of another arrangement of pixel elements, electrodes and reference elements, modified as compared to the embodiment of FIG. 3;

FIG. 3b is another modification of the embodiment of FIG. 3a;

DETAILED DESCRIPTION OF THE PREFERRED EMBODIMENTS

Figure 1:
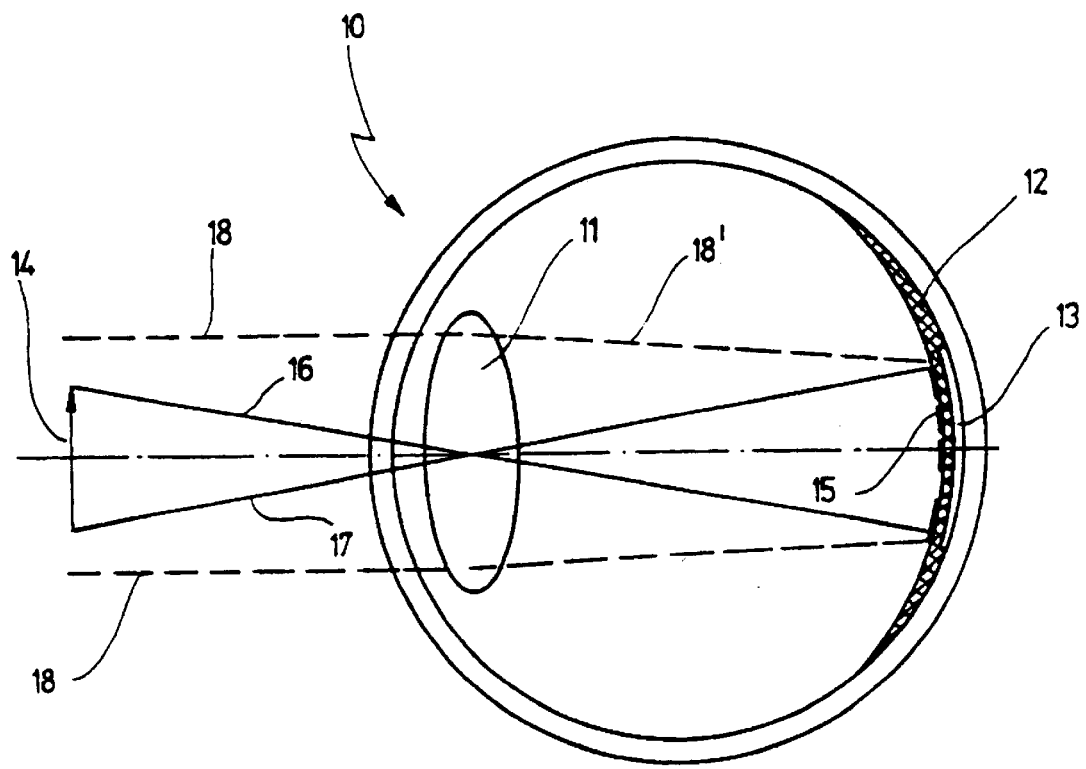
FIG. 1 shows a highly schematic cross-sectional view of an eye, the retina of which is provided with an implant according to the present invention.

In FIG. 1, reference numeral 10 as a whole designates an eye, for example a human eye. A lens 11 and a retina 12 are schematically indicated within eye 10.

A subretinal implant may be seen at 13. Implant 13 is disposed within the lower layers of retina 12.

An object 14 is conventionally reproduced on retina 12 through lens 11, as indicated with rays 16, 17 and an upside down image 15.

Reference numeral 18 in FIG. 1 indicates a bundle of rays of an invisible light, for example an infrared light. Bundle of light 18 is set such as to fall on implant 13 over its entire surface. For that purpose, bundle of light 18 is only slightly modified by lens 11, as indicated at 18' within eye 10. Such an option for externally coupling energy into the eye for supplying current to retina implant 13 is substantially known from WO 98/17343.

Figure 2:
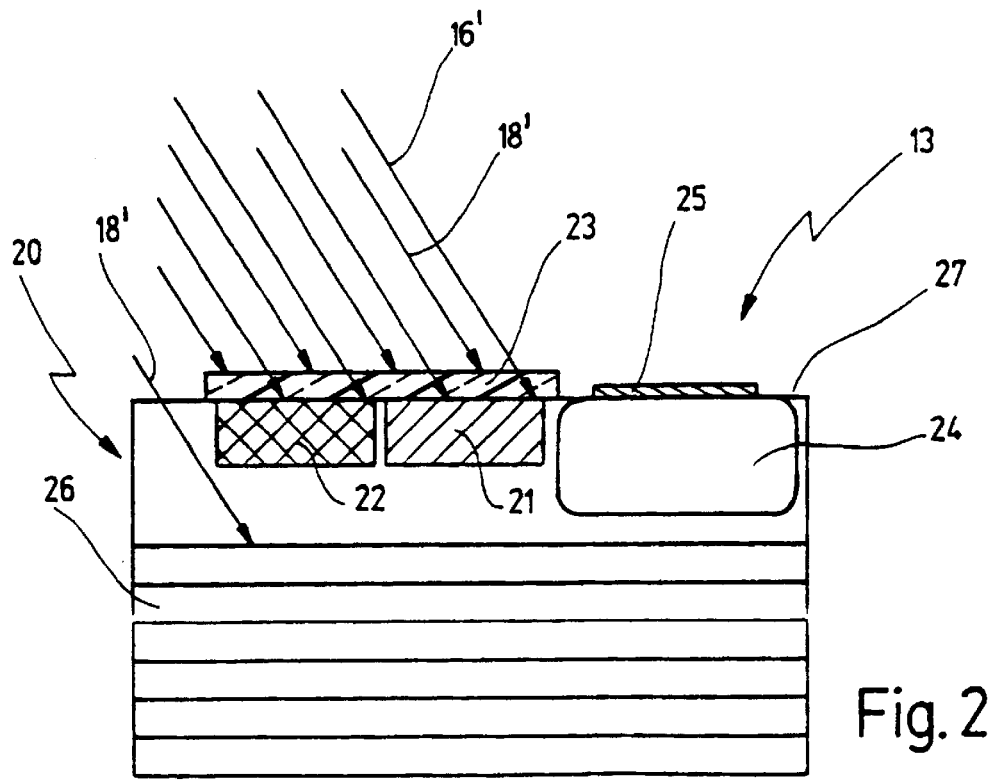
FIG. 2 shows a schematic depiction of a section of a conceivable embodiment of the inventive retina implant in subretinal design, on a highly enlarged scale and in a cross-sectional view.
Figures 3, 3A, 3B:
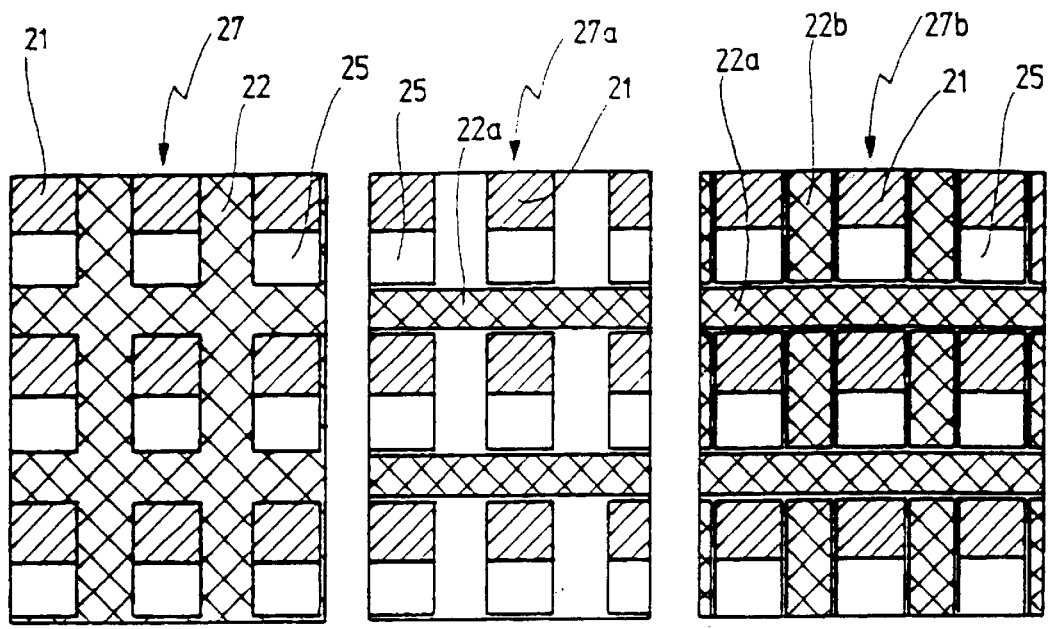
Figure 4:
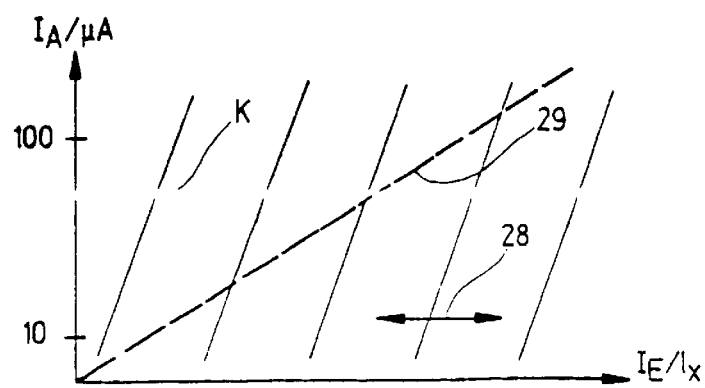
FIG. 4 is a schematic depiction of the principle underlying the invention with reference to the shifting of an amplifier characteristic curve as a function of the mean light intensity.

Implant 13 according to the invention is characterized by a particular design and structure, as may be seen as an example from subsequent FIGS. 2 through 4.

It goes without saying that the option described herein for coupling energy through infrared energy for the purpose of supplying current, shall not be understood as a limitation because any known other options for coupling energy may also be used, i.e. in particular the option for inductively coupling rf energy.

A plurality of light-sensitive pixel elements are disposed on the active surface 27 of implant 13 facing lens 11. Pixel elements 21 convert the incoming light energy, indicated in FIG. 2 as an example by arrows 16', into corresponding electric signals.

The incoming infrared radiation, indicated as an example at 18', has the purpose of establishing a current supply and will be converted into electric energy by way of an underlying infrared photodiode stack serving as a supply for an amplifier circuit 24. Amplifier circuit 24 controls a stimulating electrode 25 as a function of the incoming light energy, for stimulating the adjacent retina cells.

According to the invention, at least one light-sensitive reference element 22 is provided in addition to the light-sensitive pixel element 21. Reference element 22 is schematically shown in FIG. 2 next to pixel element 21.

Whereas in prior art arrangements according to WO 98/17343 the electrical signal received by a pixel element is directly converted into a corresponding stimulating signal of stimulating electrode 25, it is now taught to determine an average light intensity with the assistance of reference element 22 over a predetermined selected portion of surface 27. The mean light intensity is used for adjusting the characteristic curve of the amplifier. Stimulating electrode 25 is supplied via the amplifier.

In the embodiment of FIG. 2, reference element 22 and pixel element 21 are, further, covered by a filter 23 blocking away infrared radiation 18', as known per se.

Again, it should be emphasized that this embodiment shall only be understood as an example and, as an alternative, also the principle of selective absorption (i.e. without an additional filter layer) could be used or even entirely other kinds of coupling energy could be used.

The basic principle of the invention may be taken in further detail from FIG. 4 independent of this arrangement.

In FIG. 4, the output current intensity $I_A$ of an output signal discharged from a stimulating electrode 25 is depicted as a function of the incoming light intensity $I_E$ given in lux.

While a conventional arrangement, for example, according to U.S. Pat. No. 4,628,933 could have an approximately linear characteristic curve, as indicated in FIG. 4 by a dashed line 29, the invention teaches to adapt to varying light conditions, i.e. to shift characteristic curve K of amplifier 24 as a function of the mean light intensity, as registered by reference element 22, as indicated by an arrow 28. A low mean light intensity results in a shifting of characteristic curve K to the left hand side, whereas a high average light intensity will result in a shift of characteristic curve K to the right hand side.

This may be effected quite simply in that amplifier 24 determines the signal difference between pixel element 21 and reference element 22 and amplifies same. Reference element 22, thereby, determines the range of operation of the circuit so that within the pixel element the output signal of amplifier 24 only depends on how much the light intensity of pixel element 21 deviates from the light intensity of reference element 22. It goes without saying that, therefore, either reference element 22 has a larger surface than pixel element 21 and/or a plurality of reference elements 22 is utilized for determining the average light intensity.

Of course, the amplification must insofar not be restricted to the current intensity or the voltage but may also be applied to other units derived from these units, wherein the amplification may be low or may be quite high, up to 10,000 or more. Accordingly, amplifier 24 may be one stage or multiple stage. Moreover, the characteristic curve of amplifier 24 may depend linearly (as shown in FIG. 4) or otherwise, for example logarithmically, from the light intensity. The characteristic curve may, further, be restricted to a small brightness range or extend over up to ten brightness decades or even more. The output signal of amplifier 24 may be constant over time or may be gated by an additional circuit or other external installations. The output signal may be transmitted as a pulse sequence or as a cw signal.

As a matter of principle, each pixel element 21 may have an amplifier 24 and also a stimulating electrode 25 associated thereto in order to obtain the best possible resolution. Besides, one might also consider to couple a plurality of pixels to one amplifier 24 or to couple a plurality of pixel elements 21 to one stimulating electrode 25.

Within the structure of a retina implant 13 according to the present invention, as shown in exemplified form in FIG. 13, chip 20, having a plurality of pixel elements 21, amplifiers 24, stimulating electrodes 25 together with at least one or more reference elements 22 thereon may be manufactured in CMOS technology or by means of lithographic methods, as known per se.

As this is not the subject matter of the present invention, no further details are provided thereon.

With reference to FIGS. 3 and 3a through 3c, various conceivable arrangements of pixel elements, reference elements and stimulating electrodes will now be explained which, however, shall be understood as an example only.

FIG. 3 on a highly enlarged scale shows a schematic top plan view of a section of the active surface 27, i.e. the surface being provided with active circuit elements, i.e. with pixel elements and stimulating electrodes. Within this first embodiment, only one continuous reference element 22 is provided. Pairs of pixel elements 21 with adjoining stimulating electrodes 25, are disposed thereon. Below reference element 22, an associated amplifier 24 is provided. The structure is arranged on a grid pattern in regular intervals. The respective pixel elements 21 and stimulating electrodes 25 are, of course, electrically isolated relative to reference element 22 in order to avoid malfunctions of pixel elements 21 and stimulating electrodes 25.

In the embodiment of FIG. 3a, stripe-shaped reference elements 22a are disposed on the active surface 27a over a selected portion of active surface 27a. Pairs of pixel elements 21 and stimulating electrodes 25 with associated amplifier 24 are disposed between neighbored stripe-shaped reference elements 22, thus configuring gaps between neighbored pairs.

Insofar, one reference element 22 each with a plurality of pixel elements 21 is coupled via the respective associated amplifier 24.

FIG. 3b shows schematically another arrangement of pixel elements 21 and reference elements 22a, 22b. Again, stripe-shaped reference elements 22a are disposed with regular gaps between each other on the active surface 27b over a selected partial area of the active surface 27 and pairs of pixel elements 21 and stimulating electrodes 25 each are disposed between these stripe-shaped reference elements 22a, configuring gaps there-between and laterally to each other. One further rectangular reference element 22b is provided between neighbored pairs of pixel elements 21 and stimulating electrodes 25.

Insofar, a number of variations of the circuitry of reference elements 22a, 22b and amplifiers 24 is possible.

Figure 3C:
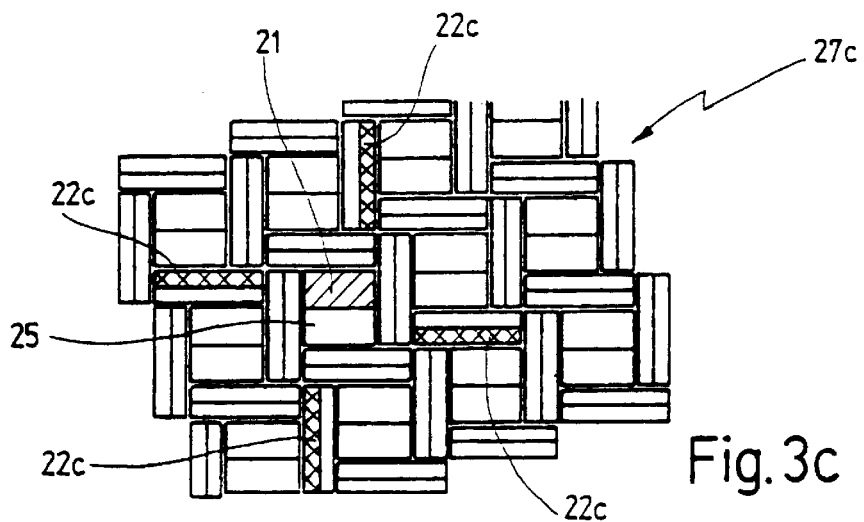
FIG. 3c is another modification of the embodiment of FIG. 3b.

FIG. 3c shows another example of an embodiment of the arrangement of pixel elements 21, stimulating electrodes 25 with associated amplifier 24 and reference elements 22c.

A plurality of reference elements 22c is distributed over active surface 27c along a chessboard pattern and over a selected portion of surface 27c. Insofar, one pixel element 21 each is connected with a stimulating electrode 25 to be a pair having a square surface and being surrounded by one pair of reference elements 22c each. Individual reference elements 22c are narrower, however, have a larger length so that entirely four pairs of reference elements 22c are disposed around a square configured by pixel element 21 and its associated stimulating electrode 25 with lateral overmeasure. Accordingly, another closed square is configured as a contour by the pairs of reference elements 22c. Insofar, the outer sides of a pair of reference elements 22c each with neighbored pairs of reference elements 22 and pairs of pixel elements 21 and stimulating electrodes 25 may again be combined as squares which are arranged offset relative to the afore-mentioned square.

Seen as a whole, a regular pattern of pixel elements 21, stimulating electrodes 25 and reference elements 22c is configured in which a square each, consisting of pixel element and stimulating electrode 25 is surrounded by the entirety of four pairs of reference elements 22c extending with a lateral overmeasure over the square and supplementing each other to a larger square.

The association between the various pixel elements 21 and the reference elements 22 may now be varied in different ways, in order to provide different variations for the determination of the average light intensity.

In FIG. 3c, as an example, the entirety of four reference elements 22c is designated with an array pattern which, together with a central pair of pixel element 21 and stimulating electrode 25 configurate a star-shaped pattern with pixel element 21 and stimulating electrode 25 in its square-shaped center together with four radially extending, thin rectangular reference elements 22c being angularly offset by 90° each. In this circuitry, the four reference elements 22c may be associated to amplifier 24 of a pixel element 21. By doing so, the output signal of stimulating electrode 25 may be controlled via the associated amplifier 24 as a function of an average light intensity being determined in the vicinity of pixel element 21 over a certain limited surrounding. Moreover, one might consider to utilize these reference elements 22c also for controlling a plurality of stimulating electrodes 25. These reference elements 22c or another partial amount of the depicted reference elements 22c may be utilized for determining light intensity for the entire chip 20 or for a partial area thereof.

By doing so, chip segments are generated which utilize the entire surface of chip 20 for determining the average light intensity, however, if a reference element should fail, only a part of chip 20 would lose its function.

In a variation of the embodiment described before, it would be possible in principle to utilize pixel elements 21 itself as reference elements 22. For that purpose, the signals received by pixel elements 21 would have to be integrated periodically for determining an average value, the average value would have to be stored and utilized for controlling the amplification as a function of the stored average value. The averaging would then have to be repeated in predetermined time intervals.

With such an arrangement, the resolution could still be increased and the structure of chip 20 could be simplified, respectively, because reference elements 22 would become obsolete, however, this would require that additional means be provided for averaging, storing and clocking. Moreover, the implants would not be active at those moments in time when the averaging and the processing of the signals received by the pixel elements would be conducted, thus resulting in a certain dead time.

However, such an arrangement would be possible by principle.

What is claimed is:

1. A retina implant comprising:
   a) a surface;
   b) a plurality of pixel elements disposed on the surface for receiving and converting incoming light energy into electrical energy;
   c) at least one amplifier in communication with the pixel elements;
   d) a plurality of stimulation electrodes, the electrodes being supplied via the at least one amplifier as a function of the incoming light energy received by the pixel elements; and
   e) at least one light-sensitive reference element coupled with the at least one amplifier for controlling amplification thereof as a function of light energy impinging on the at least one reference element.

2. The retina implant of claim 1, wherein a common reference element is provided extending over a selected portion of said surface, said pixel elements being disposed on said reference element as isolated areas.

3. The retina implant of claim 2, wherein said pixel elements are disposed on said reference element along a grid pattern.

4. The retina implant of claim 1, wherein a plurality of reference elements is distributed over a selected portion of said surface along a predetermined pattern between said pixel elements.

5. The retina implant of claim 4, wherein said reference elements are distributed over a selected portion of said surface as stripes.

6. The retina implant of claim 5, wherein further reference elements are disposed between individual stripes and pixel elements.

7. The retina implant of claim 4, wherein said reference elements are distributed over a selected portion of said surface as an oblique grid.

8. The retina implant of claim 4, wherein one reference element each is associated to a plurality of pixel elements.

9. The retina implant of claim 4, wherein each pixel element has one reference element associated thereto.

10. The retina implant of claim 4, wherein one pixel element has a plurality of reference elements associated thereto.

11. The retina implant of claim 1, wherein each pixel element has an amplifier and a stimulation electrode associated thereto.

12. The retina implant of claim 11, wherein a plurality of reference elements is distributed over a selected portion of the surface in a chessboard pattern, each pixel element being surrounded by a plurality of reference elements arranged at an angle with respect to each other.

13. The retina implant of claim 1, wherein said at least one amplifier amplifies a difference between output signals of said pixel elements and of reference elements associated thereto, and controls associated stimulation electrodes as a function of said amplified signals.

14. The retina implant of claim 1, wherein the pixel elements and the at least one reference element have the same wavelength sensitivity.

15. The retina implant of any of claim 1, wherein said pixel elements and said at least one reference element are configured as photodiodes.

16. The retina implant of claim 1, wherein said pixel elements as well as said at least one reference element each have a predetermined surface facing said incoming light, said surface of said reference element being larger than a surface of said pixel element associated thereto.

17. The retina implant of claim 1, wherein said pixel elements as well as said at least one reference element each have a predetermined surface facing said incoming light, a sum of said surfaces of a plurality of reference elements being larger than a surface of said pixel element associated thereto.

18. The retina implant of claim 1, wherein said pixel element and said at least one reference element are configured as different components.

19. The retina implant of claim 1, wherein said pixel elements and said at least one reference element are each the same component.

20. A retina implant comprising:
a plurality of pixel elements disposed on a first surface of a substrate wherein the substrate is adapted to be positioned such that the first surface faces the lens of an eye so as to receive incident light;
at least one amplifier in communication with the pixel elements and receiving external power;
plurality of stimulation electrodes positioned on the first surface so as to stimulate adjacent retinal cells of the eye; and
at least one light-sensitive reference element receiving incident light wherein the amplifier controls the stimulus of the stimulation electrodes as a function of the intensity of the incident light to the pixel elements and the at least one reference element.

21. The retina implant of claim 20, wherein the external power comprises incident electro-magnetic radiation.

22. The retina implant of claim 21, wherein the external power comprises incident electro-magnetic radiation of a range of wavelengths at least partially outside the range of wavelengths of visible light.

23. The retina implant of claim 21, further comprising a filter interposed between the pixel elements and the at least one light-sensitive reference element wherein the filter substantially passes visible light and at least partially blocks electro-magnetic radiation of wavelengths outside those of visible light.

24. The retina implant of claim 20, wherein the at least one reference element comprises a sample of the incident light received by at least one of the pixel elements.

25. A retina implant comprising:
a plurality of pixel elements disposed on a first surface of a substrate wherein the substrate is adapted to be positioned such that the first surface faces the lens of an eye so as to receive incident light;
at least one amplifier in communication with the pixel elements and receiving external power;
a plurality of stimulation electrodes positioned on the first surface so as to stimulate adjacent retinal cells of the eye; and
at least one reference element in communication with at least one of the pixel elements and the at least one amplifier wherein the at least one reference element receives at least a periodic signal representative of the intensity of the incident light received by the at least one pixel element and provides a control signal to the at least one amplifier as a function of the intensity of the incident light as received by the pixel elements and the at least one reference element.

26. A retina implant comprising:
at least one pixel element that is adapted to be implanted in an eye so as to receive light incident on the eye, wherein the pixel element produces a pixel intensity signal; and
at least one reference element that is adapted to be implanted in the eye so as to receive light incident on the eye, wherein the at least one reference element is adapted to determine an average intensity value of the light incident on the eye and wherein the retina implant produces stimulation signals as a function of the pixel intensity signal and the average intensity value.

27. The retina implant of claim 26, further comprising an amplifier receiving the pixel intensity signal and the average intensity value and producing the stimulation signals as a function thereof.

28. The retina implant of claim 27, further comprising at least one stimulation electrode positioned so as to provide the stimulation signals to the retina of the eye.

29. The retina implant of claim 26, wherein the retina implant receives external power.

30. The retina implant of claim 29, wherein the external energy comprises incident electromagnetic radiation.

31. The retina implant of claim 30, wherein the incident electromagnetic radiation is of wavelengths at least some of which are outside the wavelengths of visible light.

* * * * *

UNITED STATES PATENT AND TRADEMARK OFFICE
CERTIFICATE OF CORRECTION

PATENT NO. : 6,804,560 B2
DATED : October 12, 2004
INVENTOR(S) : Wilfried Nisch et al.

It is certified that error appears in the above-identified patent and that said Letters Patent is hereby corrected as shown below:

Title page,
Item [56], References Cited, FOREIGN PATENT DOCUMENTS, delete "09/17343" and insert -- 98/17343 --.

Column 5,
Line 14, delete "se." and insert -- sec. --.
Line 53, delete "stage." and insert -- stages. --.

Column 6,
Line 7, delete "se." and insert -- sec. --.

Signed and Sealed this

Second Day of May, 2006

JON W. DUDAS
*Director of the United States Patent and Trademark Office*